United States Patent
Papenfuhs

Patent Number: 4,613,704
Date of Patent: Sep. 23, 1986

[54] PROCESS FOR THE PREPARATION OF 5-HYDROXYETHYLSULFONYL-2-AMINO-PHENOL (ETHERS)

[75] Inventor: Theodor Papenfuhs, Frankfurt am Main, Fed. Rep. of Germany

[73] Assignee: Hoechst Aktiengesellschaft, Frankfurt am Main, Fed. Rep. of Germany

[21] Appl. No.: 675,979

[22] Filed: Nov. 29, 1984

[30] Foreign Application Priority Data

Dec. 1, 1983 [DE] Fed. Rep. of Germany ....... 3343421

[51] Int. Cl.⁴ .................... C07C 85/11; C07C 84/00
[52] U.S. Cl. .................................... 564/418; 564/440
[58] Field of Search ............................... 564/418, 440

[56] References Cited

FOREIGN PATENT DOCUMENTS

| 0092909 | 11/1983 | European Pat. Off. ............ 564/440 |
| 0931595 | 7/1963 | United Kingdom ................ 564/440 |
| 1195344 | 6/1970 | United Kingdom . |
| 1540566 | 2/1979 | United Kingdom . |

*Primary Examiner*—Charles F. Warren
*Assistant Examiner*—John A. Sopp
*Attorney, Agent, or Firm*—Connolly and Hutz

[57] ABSTRACT

Process for the preparation of 5-hydroxyethylsulfonyl-2-aminophenol (ethers) of the formula (I)

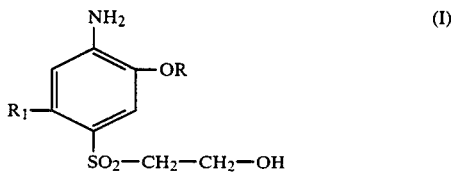

wherein R denotes a hydrogen atom or a $C_1$–$C_4$-alkyl group and $R_1$ denotes a hydrogen atom or an alkyl or alkoxy group with in each case 1–4 carbon atoms, which comprises condensing 5-chloro(or bromo)-2-nitrophenols, or alkyl ethers thereof, of the formula (II)

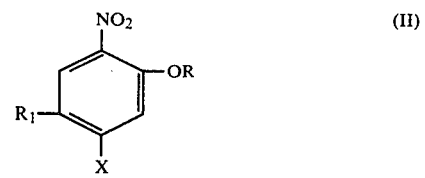

in which R and $R_1$ have the abovementioned meanings and X denotes a chlorine or bromine atom, with thioglycol to give 2-nitrophenol(ether) 5-hydroxyethyl-sulfides of the formula (III)

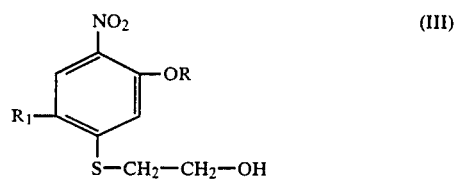

wherein R and $R_1$ have the abovementioned meanings, oxidizing these to give 5-hydroxyethylsulfonyl-2-nitrophenol (ethers)

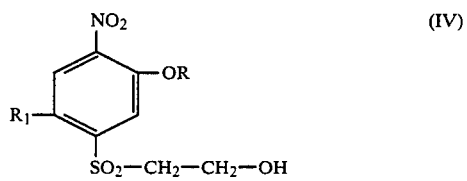

and reducing the latter to give compounds of the above formula (I).

3 Claims, No Drawings

PROCESS FOR THE PREPARATION OF 5-HYDROXYETHYLSULFONYL-2-AMINO-PHENOL (ETHERS)

The present invention relates to an industrially advantageous process, which comprises only a few stages and pollutes the environment less than the known process, for the preparation of 5-hydroxyethylsulfonyl-2-aminophenol (ethers) of the general formula (I)

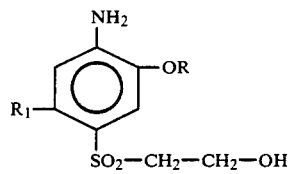

in which R denotes a hydrogen atom or an alkyl group with 1–4 carbon atoms and $R_1$ denotes a hydrogen atom or an alkyl or alkoxy group with in each case 1–4 carbon atoms.

5-Hydroxyethylsulfonyl-2-aminophenol (ethers) of the abovementioned general formula (I) are important dyestuff intermediates and are used, in particular, for the preparation of reactive dyestuffs. 5-Hydroxyethylsulfonyl-2-aminophenol ($R=R_1=H$) has hitherto been prepared industrially from o-aminophenol, which is cyclized with urea to give benzoxazoles (protection of the amino and hydroxyl function), the benzoxazole is sulfochlorinated with excess chlorosulfonic acid (if appropriate in the presence of thionyl chloride), the sulfonation product is then reduced with bisulfite/sodium hydroxide solution and the reduction product is condensed with ethylene oxide, and, finally, the product is converted into 5-hydroxyethylsulfonyl-2-aminophenol (or its sulfate ester) by cyclization hydrolysis by means of sulfuric acid, in accordance with the following equation:

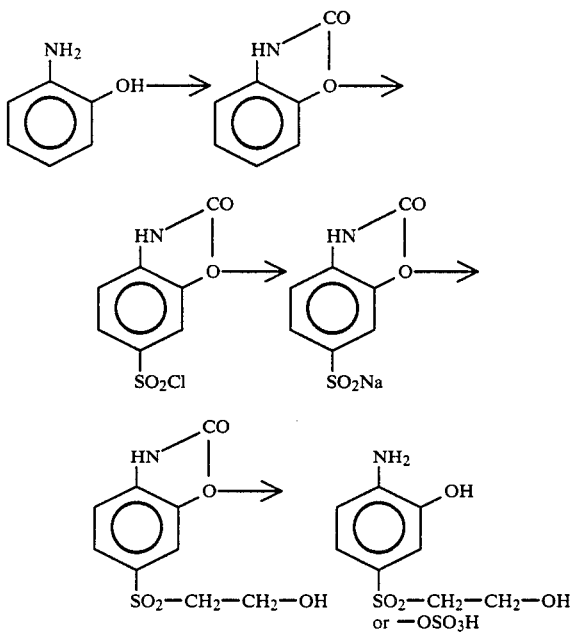

The corresponding phenol ethers (R=alkyl in formula I) have hitherto been prepared industrially by acylation of the amine on which they are based, followed by the subsequent reactions described above, carried out in an analogous manner, so that, finally, the 5-hydroxyethylsulfonyl-2-aminophenol ethers (or their sulfate esters) are obtained in accordance with the following equation:

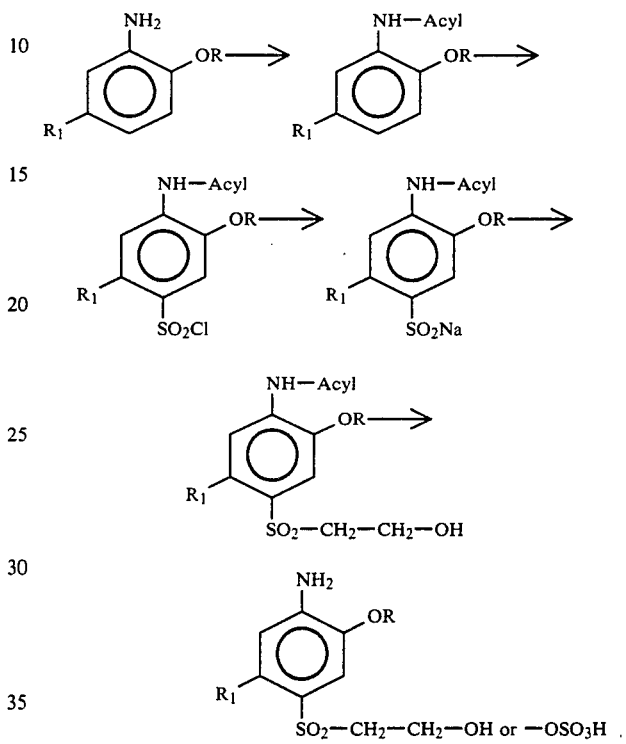

These multi-stage processes are very expensive industrially, usually require special apparatuses and are distinguished by high pollution of the effluent (hydrochloric acid and sulfuric acid from the sulfochlorination, salts from the sulfite reduction, ethylene oxide secondary products). They are therefore not economical.

As a result, there was the object of rendering these important dyestuff intermediates accessible via more economic routes in an industrially advantageous synthesis which comprises only a few stages and pollutes the environment less.

This object is achieved by the present invention, by condensing the 5-chloro(or bromo)-2-nitrophenols, or their alkyl ethers, which are readily accessible industrially by partial hydrolysis or alcoholysis of 2,4-dichloro- or -dibromo-nitrobenzenes, and the 5-chloro(or bromo)-2-nitrohydroquinine dialkyl ethers which are industrially available in high yields by nitration oof halogenohydroquinone dialkyl ethers, with thioglycol to give 2-nitrophenol(ether)-5-hydroxyethyl-sulfides and oxidizing these, with or without, preferably without, intermediate isolation, to 5-hydroxyethylsulfonyl-2-nitrophenol (ethers). Final reduction of the nitro group gives a high yield and quality of the required target products of the formula (I) in a minimum number of synthesis stages.

The present invention thus relates to a process for the preparation of 5-hydroxyethylsulfonyl-2-aminophenol (ethers) of the general formula (I)

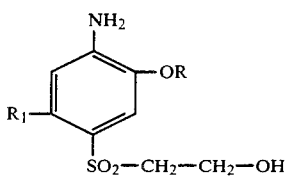

in which R denotes a hydrogen atom or an alkyl group with 1–4 carbon atoms and $R_1$ denotes a hydrogen atom or an alkyl or alkoxy group with in each case 1–4 carbon atoms, which comprises condensing 5-chloro(or bromo)-2-nitrophenols or their monoalkyl ethers of the general formula (II)

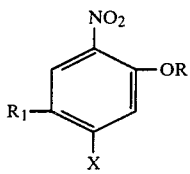

in which R and $R_1$ have the abovementioned meanings and X denotes a chlorine or bromine atom, with thioglycol to give 2-nitrophenol(ether) 5-hydroxyethyl-sulfides of the formula (III)

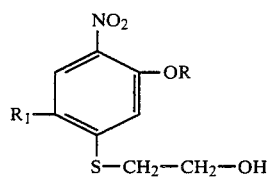

in which R and $R_1$ have the abovementioned meanings, oxidizing these compounds, with or, preferably, without intermediate isolation, to give 5-hydroxyethylsulfonyl-2-nitrophenol (ethers) of the formula (IV)

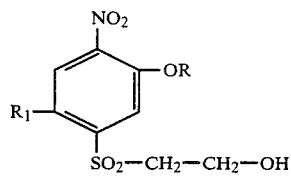

and reducing the latter to give the compounds of the above formula (I).

The reaction of halogen atoms activated by nitro groups with thioglycol to give nitroaryl-hydroxyethyl-sulfides is indeed known in principle (cf. German Offenlegungsschrift No. 3,135,367) and, in the case of o-nitrohalogenobenzenes, gives high yields. However, with the p-isomers, an unpredictable reaction is reported (cf. J. Chem. Soc. 1927, 1668), which in an optimum procedure (according to German Offenlegungsschrift No. 3,135,367) gives the desired 4-nitro-hydroxyethyl-sulfide, although with moderate yields (60–75%), as long as dipolar aprotic solvents (dimethylformamide, dimethylacetamide, N-methylpyrrolidone or N-methylimidazolidinone), which are industrially unfavorable since they are expensive to regenerate industrially, are not used.

It was therefore surprising and not to be foreseen that p-nitro-halogenobenzenes which are even more unfavorably substituted by halogen-deactivating groups (alkyl, alkoxy or hydroxyl groups ) (cf. formula II) can be condensed with thioglycol to give high yields and purities of the required thioethers of the formula (III) even in the absence of any solvent, i.e. in aqueous solution of suspension.

The oxidation of aryl-alkyl thioethers to give the corresponding sulfones is also known in principle (cf. German Pat. No. 944,607, oxidizing agent: hypochlorite in alkaline solution; Japanese published patent application No. 24.661/68, oxidizing agent: hydrogen peroxide in the presence of bicarbonates; German Offenlegungsschrift No. 3,135,367, oxidizing agent: hydrogen peroxide in the presence of catalytic amounts of tungstic acid). The use of the oxidation processes known from German Pat. No. 944,607 and Japanese published patent application No. 24.661/68, which proceed in an alkaline medium, does not lead at all to the target product when the thioethers of the formula (III) selected according to the invention are employed. Without exception, decomposition and/or oxidation products of the starting compounds are obtained in an unpredictable reaction. The required 5-hydroxyethylsulfonyl-2-nitrophenol (ethers) of the formula (IV) are never formed in amounts which can be isolated. A similarly disheartening result is obtained if the process known from German Offenlegungsschrift No. 3,135,367 is carried out at pH values >6 (a pH range from 3 to 8 is claimed).

In contrast, a smooth oxidation of the thioethers of the formula (III) to give a high yield of hydroxyethylsulfones of the formula (IV) is obtained if the reaction with hydrogen peroxide is carried out in the presence of catalytic amounts of tungstic acid in a pH range from 4 to 6. This drastic change in the course of the oxidation with only a slight change in pH is already surprising per se. However, it is even more surprising that phenols and phenol ethers, as the compounds of the formula (III) without exception are, can be reacted with $H_2O_2$ under certain reaction conditions without hydroxylation of the nucleus. In fact, it was to be expected that, in the manner known from the literature (cf. Houben-Weyl 6, 1c, page 30 et seq.), when hydrogen peroxide acts on hydroxy- or alkoxy-phenylhydroxyethyl-sulfides (formula III), hydroxylation of the phenyl nucleus takes place, in addition to or instead of the oxidation of the sulfur bridge, which means that unpredictable product mixtures and hence unsatisfactory yields would result. In addition, hydrolysis of the alkoxy group in the o-position relative to the nitro group in the thioethers of the formula (III) (R=alkyl) was also not to be excluded from the start on reaction in systems containing water.

Such side reactions are assumed probably to proceed simultaneously and/or consectively in a pH-dependent manner, including the case of the reaction of the thioethers of the formula (III) with hydrogen peroxide, and in pH ranges <4 and >6 lead, inter alia, to completely unpredictable reaction sequences, which makes achievement of the aim of optimizing uniform isolation of the required end products of the formula (IV) seem less probable.

It was therefore all the more surprising that it is possible to carry out the required oxidation of the thioether bridge in 2-nitrophenol(ether) 5-hydroxyethylsulfides (formula III) selectively and completely in the pH range of 4 to 6 in aqueous solution or suspension and to obtain a high yield of the required 5-hydroxyethylsulfonyl-2-nitrophenol (ethers) (formula IV) in the tungstate-catalyzed reaction of these compounds of the formula (III) with at least the stoichiometric amount (2 moles) of hydrogen peroxide.

When starting substances containing hydroxyl groups (formula II, R=H) are used, the pH range according to the invention excludes elimination of the deactivating effect of the OH group by salt formation, so that the smooth course of the oxidation was even less to be expected at all. For the target products claimed, the process according to the invention is thus novel, surprising and economically and ecologically superior to the prior art, and thus represents a considerable technical advance.

Specifically, the process is carried out by heating a p-nitro-halogenobenzene substituted according to formula (II) to temperatures of 50°-90° C., preferably 65°-80° C., together with at least a stoichiometric amount of thioglycol and, if appropriate, water (to achieve adequate stirrability in each phase of the reaction), and then introducing, in the course of 1-5 hours, preferably 2-3 hours, portions of at least a stoichiometric amount of an acid-binding alkali metal compound or alkaline earth metal compound, such as, for example, an alkali metal oxide, hydroxide or carbonate or alkaline earth metal oxide, hydroxide or carbonate, preferably sodium carbonate or, in particular, potassium carbonate (if compounds of the formula (II) in which R=H are used, 1 mole of carbonate per mole of compound of the formula (II), if compounds of the formula (II) where R≠H are used, 0.5 mole of carbonate per mole of compound of the formula (II)). The mixture is then subsequently stirred until the reaction has ended (monitoring by thin layer chromatography or HPLC) (HPLC=high performance liquid chromatography analysis) (3-10 hours) and a pH value of 4-6 is then adjusted by running in an acid (mineral acid or acetic acid). The 2-nitrophenol(ether) 5-hydroxyethyl-sulfide formed (formula III) can be isolated in a high yield by filtration, after cooling to room temperature. However, it is more advantageous to add at least the stoichiometric amount of hydrogen peroxide (2 moles per mole of compound of the formula III) to the resulting suspension after addition of catalytic amounts of tungsten trioxide or alkali metal tungstate (1-10 g per mole of starting compound of the formula (II)) and, if appropriate, after dilution with water and, after the oxidation has ended (monitoring by TLC (=thin layer chromatography) or HPLC, after-stirring time about 2-6 hours), to crystallize the product of the formula IV out of the resulting solution or suspension by cooling to 0°-20° C. and subsequently to isolate it by filtration.

The final reduction of the nitro group is not critical. It can be carried out by known methods, for example by reduction with iron or catalytic reduction on nickel catalysts or noble metal catalysts in an aqueous system, and gives an excellent quality and yield of the target products (formula I).

The individual stages of the process according to the invention can of course be carried out in isolation or combination in the presence of customary solvents or diluents, if these are sufficiently stable under the reaction conditions. However, the advantage of a particularly simple process procedure in a purely aqueous system and hence in apparatuses which are usual in industry is thereby partly lost (solvent filtration and/or regeneration in special apparatuses), and additional costs arise due to solvent loss, without having a positive influence on the yield and/or quality. Such a procedure is therefore not preferred.

The following examples are intended to illustrate the process in more detail, without restricting it thereto.

EXAMPLE 1

A mixture of 347 parts of 5-chloro-2-nitrophenol, 300 parts of thioglycol and 200 parts of water is heated to 70°-75° C., and 350 parts of solid potassium carbonate are added in portions at this temperature in the course of 3 hours, with stirring and exclusion of oxygen. The mixture is subsequently stirred for 6-8 hours, until no further starting substance can be detected by thin layer chromatography monitoring, and is cooled to room temperature and the pH is brought to 4 by dropwise addition of about 425 parts of 30% strength hydrochloric acid, whereupon the 2-nitrophenol 5-hydroxyethyl-sulfide precipitates in the form of yellow crystals. The product is isolated at 10°-15° C. by filtration by suction on a filter and is washed until neutral and dried in vacuo at 50°-60° C. to give 394 parts of 2-nitrophenol 5-hydroxyethyl-sulfide of melting point 85°-86° C., corresponding to a yield of 91.6% of theory, based on the 5-chloro-2-nitrophenol.

The product is chromatographically pure, and shows the values corresponding to its structure in elemental analysis (calculated: $NO_2$: 21.4%; S: 14.9%; OH: 7.9%; and Cl: 0.0%; found: $NO_2$: 21.4/21.5%; S: 15.0%; OH: 7.9/8.1%; and residual Cl: 0.012%).

If the corresponding amounts of sodium carbonate are used instead of potassium carbonate, the introduction time and subsequent stirring time must be prolonged by about 50%, in order to obtain a comparable result.

EXAMPLE 2

175 parts of potassium carbonate are uniformly added to a mixture of 435 parts of 5-chloro-2-nitrohydroquinone dimethyl ether, 200 parts of thioglycol and 200 parts of water at 55°-60° C. in the course of 3 hours, with stirring and exclusion of oxygen, and the mixture is then subsequently stirred at 60° C. for 12-15 hours until monitoring by thin layer chromatography indicates that the reaction is complete. The mixture is cooled to room temperature and the yellow precipitate is filtered off with suction on a filter. After washing until neutral and drying at 60°-80° C. in vacuo, 480 parts of 2-nitrohydroquinine dimethyl ether 5-hydroxyethyl-sulfide of melting point 112°-113° C. are obtained, corresponding to a yield of 92.6% of theory, based on the 5-chloro-2-nitrohydroquinone dimethyl ether. The product is chromatographically pure and shows the values corresponding to its structure is elemental analysis (calculated: $NO_2$: 17.8%; S: 12.4; $OCH_3$: 23.9% and Cl: 0.0%; found: $NO_2$: 18.0/17.8%; S: 12.4%; $OCH_3$: 23.6/23.8%; and residual Cl: 0.005%).

EXAMPLE 3

If the 5-chloro-2-nitrohydroquinone dimethyl ether in Example 2 is replaced by an aliquot amount of 5-chloro-2-nitrohydroquinone diethyl ether and the mixture is otherwise worked up in the manner indicated, 260 parts of 2-nitro-hydroquinone diethyl ether 5-hydroxyethyl-sulfide of melting point 108°-110° C. is obtained in a somewhat poorer quality (residual Cl content: 0.3-0.4%), which can be used as such, without restriction, for oxidation. The yield, based on the 5- chloro-2-nitrohydroquinone diethyl ether employed, is 90.8% of theory.

EXAMPLE 4

An aqueous solution, saturated at 80° C., of 175 parts of potassium carbonate is uniformly added dropwise to a mixture of 403 parts of 2-chloro-5-nitro-p-cresol methyl ether, 185 parts of thioglycol and 220 parts of water at 75°–80° C. in the course of 5 hours, with stirring and exclusion of oxygen. The mixture is subsequently stirred at 80°–85° C. until the reaction has ended (4–6 hours, monitoring by thin layer chromatography) and is cooled to room temperature and the yellow precipitate which has separated out is isolated on a suction filter. After washing until neutral and drying in vacuo at 60° C., 432 parts of 3-nitro-4-methoxytoluene 6-hydroxyethylsulfide of melting point 98°–99° C. are obtained, corresponding to a yield of 88.8% of theory, based on the 2-chloro-5-nitro-p-cresol methyl ether. The product is almost chromatographically pure and can be used as such, without restriction, for subsequent oxidation (residual Cl content: 0.2–0.25%).

EXAMPLE 5

A mixture of 215 parts of 2-nitrophenol 5-hydroxyethyl-sulfide, 4 parts of sodium tungstate dihydrate and 1,000 parts of water is brought to pH 5–5.5 at 60° C. with 20% strength acetic acid, and 117 parts of 30% strength hydrogen peroxide are then added in the course of 30 minutes, the internal temperature simultaneously being increased to 80° C. A further 152 parts of 30% strength hydrogen peroxide are then uniformly added dropwise at 80°–90° C. in the course of another hour, a clear, almost colorless solution being formed. The mixture is subsequently stirred at 90°–95° C. for 3 hours (monitoring for complete reaction by thin layer chromatography) and is then cooled to 10°–15° C., with stirring. The crystals which thereby separate out are filtered off with suction, covered twice with water and dried at 60°–80° C. in vacuo.

234 parts of 5-hydroxyethylsulfonyl-2-nitrophenol of melting point 140°–142° C. are obtained, corresponding to a yield of 94.7% of theory, based on the starting substance.

The compound is chromatographically pure and corresponds to the given structure in elemental analysis (calculated: $NO_2$: 18.6% and S: 13.0%, found: $NO_2$: 18.6/18.6% and S: 12.7%).

EXAMPLE 6

100 parts of 35% strength hydrogen peroxide are added dropwise, in the course of 1 hour at 70°–75° C., to a stirred mixture of 229 parts of 2-nitroanisole 5-hydroxyethyl-sulfide, melting point 95°–96° C. (prepared analogously to Examples 1–4 using 2-nitro-5-chloranisole), 4.5 parts of potassium tungstate and 1,200 parts of water, which has been brought to pH 4.5–5 with 2N hydrochloric acid. The mixture is heated to 90°–95° C. in the course of 30 minutes and a further 110 parts of 35% strength hydrogen peroxide are added dropwise in the course of 90 minutes, the mixture is subsequently stirred at this temperature for 3–4 hours (monitoring for complete reaction by HPLC) and is then cooled to 20°–25° C. and the yellowish-white precipitate which has separated out is isolated by filtration on a suction filter. The product is covered twice with water, sucked dry and dried in vacuo at 60°–70° C. 250 parts of 5-hydroxyethylsulfonyl-2-nitroanisole of melting point 106°–108° C. result, corresponding to a yield of 95.8% of theory, based on the starting substance.

The compound is chromatographically pure and shows values corresponding to its structure in elemental analysis (calculated: $NO_2$: 17.6%; and S: 12.3%; found: $NO_2$: 17.5%; and S: 12.0/12.3%).

EXAMPLE 7

90 parts of 80% strength hydrogen peroxide are uniformly added to a mixture, brought to pH 5–5.5 with 20% strength phosphoric acid, of 518 parts of 2-nitrohydroquinone dimethyl ether 5-hydroxyethyl-sulfide, 2,500 parts of water and 6 parts of tungsten trioxide at 55°–60° C. in the course of 45 minutes, with stirring, during which the temperature may rise to at most 75° C. The mixture is then subsequently stirred at 75° C. for 1 hour and a further 100 parts of 80% strength hydrogen peroxide are added dropwise at this temperature in the course of another 90 minutes. The internal temperature is increased to 90°–95° C. and the reaction is brought to completion by subsequent stirring for 3–4 hours (monitoring by HPLC). The mixture is then allowed to cool and the precipitate which has separated out is filtered off with suction at 15°–20° C. on a filter, washed twice with ice-water and dried in a circulating air cabinet at 60°–70° C. 561 parts of almost colorless 5-hydroxyethylsulfonyl-2-nitrohydroquinone dimethyl ether of melting point 129°–131° C. are obtained, corresponding to a yield of 96.4% of theory, based on the starting substance.

The compound is chromatographically pure and gives values corresponding to its structure in elemental analysis (calculated: $NO_2$: 15.8% and S: 11.0%; found: $NO_2$: 16.0/15.8%, and S: 11.0%).

If the oxidation is carried out in the absence of the tungsten catalyst but otherwise in the manner described, a reaction time increased by a factor of 4 and a 10–15% higher hydrogen peroxide requirement are necessary. The quality and yield are not thereby changed.

EXAMPLE 8

152 parts of potassium carbonate are added in portions to a mixture of 173.5 parts of 5-chloro-2-nitrophenol, 110 parts of thioglycol and 100 parts of water at 80°–85° C. in the course of 5 hours, with stirring and exclusion of oxygen. The mixture is subsequently stirred for about 5–6 hours, while slowly increasing the temperature to 90° C., until no further starting substance can be detected (monitoring by thin layer chromatography), 900 parts of water and 4 parts of sodium tungstate dihydrate are added and the resulting solution is brought to pH 5–5.5 with 85% strength phosphoric acid.

210 parts of 30% strength hydrogen peroxide are subsequently added dropwise in the course of 60 minutes, starting at 60° C., during which the temperature should rise to 75°–80° C. A further 160 parts of 30% strength hydrogen peroxide are then uniformly added dropwise at 80°–90° C. in the course of another hour and the mixture is subsequently stirred at 90°–95° C. for 3–4 hours (monitoring for complete reaction by HPLC) and then cooled to 10°–15° C., with stirring. The product which thereby precipitates is filtered off with suction, washed with water until neutral and free from salts and dried in vacuo at 60°–80° C.

225 parts of 5-hydroxyethylsulfonyl-2-nitrophenol of melting point 140°–141° C. are obtained, corresponding to a yield of 91.1% of theory, based on the 5-chloro-2-nitrophenol.

EXAMPLE 9

75 parts of potassium carbonate are added in portions to a suspension consisting of 289.9 parts of 5-bromo-2-nitrohydroquinone diethyl ether, 100 parts of thioglycol and 300 parts of water at 65°–70° C. in the course of 4 hours, with stirring and exclusion of oxygen. The mixture is subsequently stirred at 70°–75° C. for 8–10 hours (monitoring for complete reaction by thin layer chromatography) and is diluted with 800 parts of water, 5 parts of potassium tungstate are added and the mixture is buffered to pH 5–5.5 with 50% strength acetic acid.

Starting at 50°–55° C., 130 parts of 35% strength hydrogen peroxide are now added dropwise in the course of 60 minutes, during which the temperature may rise to a maximum of 75° C., and the mixture is subsequently stirred at 75° C. for one hour. Thereafter, a further 120 parts of 35% strength hydrogen peroxide are added dropwise at 75° C. in the course of 90 minutes, the temperature is subsequently increased to 90°–95° C. and the mixture is subsequently stirred at this temperature until the oxidation is complete (monitoring by HPLC, time taken about 4–5 hours). The mixture is allowed to cool and the precipitate which has separated out is filtered off with suction at 15°–20° C. on a filter, washed twice with 200 parts of ice-water and dried in vacuo at 50°–65° C.

288 parts of 5-hydroxyethylsulfonyl-2-nitrohydroquinone diethyl ether of melting point 128°–130° C. are obtained, corresponding to a yield of 90.3% of theory, based on the 5-bromo-2-nitrohydroquinone diethyl ether.

EXAMPLE 10

70 parts of potassium carbonate are uniformly introduced into a mixture of 187.5 parts of 5-chloro-2-nitroanisole, 120 parts of thioglycol and 120 parts of water at 70°–75° C. in the course of 3 hours, with stirring and exclusion of oxygen. The mixture is subsequently stirred at 75°–80° C. for 6–8 hours, until no further starting substance can be detected (monitoring by thin layer chromatography), 800 parts of water, warmed to 80° C., and 3 parts of tungsten trioxide are then added and a pH value of 4–4.5 is established by dropwise addition of acetic acid. 175 parts of 30% strength hydrogen peroxide are now added dropwise at 80° C. in the course of 30 minutes, the mixture is subsequently stirred for 1 hour, while the temperature is slowly increased to 90°–95° C., and a further 150 parts of 30% strength hydrogen peroxide are then added dropwise, again in the course of 30 minutes. The oxidation is brought to completion by subsequent stirring at 90°–95° C. (monitoring by HPLC) and the product is precipitated by cooling to 20°–25° C., isolated by filtration and, after washing with water, dried in vacuo at 50°–60° C.

230 parts of 5-hydroxyethylsulfonyl-2-nitroanisole of melting point 105°–107° C. are obtained, corresponding to a yield of 92.5% of theory, based on the 5-chloro-2-nitroanisole.

EXAMPLE 11

760 parts of water are initially introduced into a hydrogenating autoclave, 98.8 parts of 5-hydroxyethylsulfonyl-2-nitrophenol and 2.5 parts of noble metal catalyst (5% strength Pd-on-charcoal) are introduced in succession and a pH value of 5.5–6 is established by addition of phosphate buffer.

The autoclave is closed and flushed with nitrogen and then hydrogen and hydrogenation is subsequently carried out under 15 bar of hydrogen pressure/50°–70° C. When no further hydrogen is absorbed, which is the case after about 60 minutes, the autoclave is let down and the mixture is clarified from the catalyst at 80° C. and cooled to 0°–5° C., with exclusion of oxygen. The mixture is filtered and the residue is washed with 50–100 parts of ice-water and dried in vacuo at 60°–70° C. 75 parts of 5-hydroxyethylsulfonyl-2-aminophenol of melting point 115°–117° C. are obtained, corresponding to a yield of 86.4% of theory, based on the nitro compound employed.

A further 6 parts of product can be precipitated from the mother liquor by addition of 10% of sodium chloride and can be isolated by filtration, so that a total yield of 5-hydroxyethylsulfonyl-2-aminophenol of 81 parts, corresponding to 93.3% of theory, results.

A comparable yield is also obtained if instead of using water in the next batch, 760 parts of the mother liquor from this batch are initially introduced and the process is otherwise carried out in the manner described.

The 5-hydroxyethylsulfonyl-2-aminophenol isolated is chromatographically pure. Its diazotization value is 99.2%. The product can be used without restrictions for the preparation of reactive dyestuffs.

EXAMPLE 12

A mixture of 200 parts of iron chips, 1,800 parts of water and 35 parts of 30% strength hydrochloric acid is heated to 95°–100° C., with stirring. 247 parts of 5-hydroxyethylsulfonyl-2-nitrophenol are then uniformly introduced in the course of 2–3 hours and the mixture is subsequently stirred at 95°–100° C. for 1 hour. The reduction has ended when the result of a spot test on filter paper is colorless. The mixture is rendered clearly alkaline to phenolphthalein with about 320 parts of 33% strength sodium hydroxide solution, the iron slurry is filtered off with suction on a heated filter and the residue on the filter is washed with 500 parts of hot 2% strength sodium hydroxide solution at 100° C. The combined filtrate is cooled to 40° C., with exclusion of oxygen, brought to a pH value of 5.0 with 30% strength hydrochloric acid and slowly cooled to 0° C. After filtration with suction and drying at 60°–70° C. in vacuo, 191 parts of 5-hydroxyethylsulfonyl-2-aminophenol of melting point 115°–116° C. are obtained, corresponding to a yield of 88.0% of theory, based on the nitro compound employed.

Further product of comparable quality can be isolated from the mother liquor by salting out. Advantageously, however, the solution obtained after clarification from the iron slurry which, according to content determination (diazotization value), contains about 98–99% of theory of 5-hydroxyethylsulfonyl-2-aminophenol, can be diazotized directly without loss and further processed to give the dyestuff. The product losses unavoidable during isolation because of the good water-solubility of 5-hydroxyethylsulfonyl-2-aminophenol can in this way be reduced to a minimum.

EXAMPLES 13–17

The 5-hydroxyethylsulfonyl-2-nitrophenol ethers accessible according to the invention (cf. Examples 6, 7, 9 and 10) are also reduced analogously to Examples 11 and/or 12, and the products listed in the following table with their melting point, purity (diazotization value) and yield isolated are obtained (almost quantitative yields are detected, by means of the diazotization value and/or by potentiometric titration, in the reduction solutions):

TABLE

| Example | Target compound of the formula I | | Yield | Purity | Melting Point |
|---|---|---|---|---|---|
| | R | $R_1$ | | | |
| 13 | $CH_3$ | $OCH_3$ | 91.2% | 99.4% | 141–144° C. |
| 14 | $CH_3$ | $CH_3$ | 91.6% | 99.0% | 84–87° C. |
| 15 | $CH_3$ | H | 89.2% | 99.0% | 180–181° C. (hydrochloride) |
| 16 | $C_2H_5$ | $OC_2H_5$ | 88.8% | 98.8% | 137–139° C. |
| 17 | $C_2H_5$ | $CH_3$ | 89.5% | 99.3% | 81–81° C. |

I claim:

1. A process for the preparation of a 5-hydroxyethyl-sulfonyl-2-aminophenol (ether) of the formula (I)

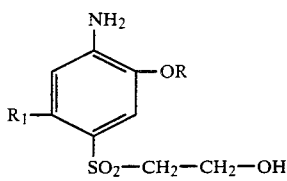

in which R denotes a hydrogen atom or an alkyl group with 1–4 carbon atoms and $R_1$ denotes a hydrogen atom or an alkyl or alkoxy group with in each case 1–4 carbon atoms, which comprises condensing with sufficient water to insure adequate stirrability a 5-chloro (or bromo)-2-nitrophenol or alkyl ether thereof of the formula (II)

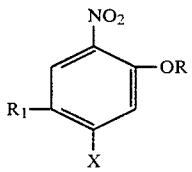

in which R and $R_1$ have the abovementioned meanings and X denotes a chlorine or bromine atom, with thioglycol to give a 2-nitrophenol(ether) 5-hydroxyethylsulfide of the formula (III)

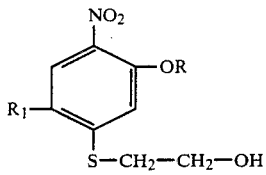

in which R and $R_1$ have the abovementioned meanings, oxidizing this product, with or without intermediate isolation, to give a 5-hydroxyethylsulfonyl-2-nitrophenol (ether) of the formula (IV)

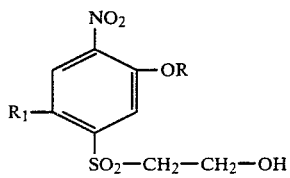

and reducing the latter to give a compond of the above formula (I).

2. The process as claimed in claim 1, wherein a p-nitrochlorobenzene compound of the formula (II) is heated to a temperature of 50°–90° C. with at least the stoichiometric amount of thioglycol, at least the stoichiometric amount of an acid-binding alkali metal compound or alkaline earth metal compound is then added in portions and, when the reaction has ended, the pH value is brought to 4–6 by means of acid.

3. The process as claimed in claim 1, wherein at least a stoichiometric amount of hydrogen peroxide is added in portions to the compound of the formula (III), obtained in suspended form, with or without intermediate isolation, after addition of catalytic amounts of tungsten trioxide or an alkali metal tungstate and, with or, after or without dilution with water, and, when the oxidation has ended, the resulting compound of the formula (IV) is separated off.

* * * * *

UNITED STATES PATENT AND TRADEMARK OFFICE
CERTIFICATE OF CORRECTION

PATENT NO. : 4,613,704
DATED : September 23, 1986
INVENTOR(S) : Theodor Papenfuhs It is certified that error appears in the above-identified patent and that said Letters Patent is hereby corrected as shown below:

In claim 3, column 12, line 42, for "with or, after" read -- with --.

Signed and Sealed this

Sixth Day of October, 1987

Attest:

DONALD J. QUIGG

Attesting Officer

Commissioner of Patents and Trademarks